(12) United States Patent
Sun

(10) Patent No.: US 7,458,932 B2
(45) Date of Patent: Dec. 2, 2008

(54) TONGUE STABILIZER FOR LARYNGOSCOPE BLADE

(76) Inventor: William Y. Sun, 205 Yoakum Pkwy., #623, Alexandria, VA (US) 22304

(*) Notice: Subject to any disclaimer, the term of this patent is extended or adjusted under 35 U.S.C. 154(b) by 724 days.

(21) Appl. No.: 10/729,973

(22) Filed: Dec. 9, 2003

(65) Prior Publication Data
US 2005/0124859 A1    Jun. 9, 2005

(51) Int. Cl.
*A61B 1/267* (2006.01)

(52) U.S. Cl. .............. 600/190; 600/185; 600/186; 600/187; 600/188; 600/189; 600/235; 600/237; 600/238; 600/239; 600/240; 600/241

(58) Field of Classification Search ......... 600/185–200, 600/235, 237–241
See application file for complete search history.

(56) References Cited

U.S. PATENT DOCUMENTS

| | | | |
|---|---|---|---|
| 2,723,661 A | 11/1955 | Hull | |
| 2,765,785 A | 10/1956 | Pagoto | |
| 4,589,848 A | 5/1986 | Inoue | |
| 4,834,077 A | 5/1989 | Sun | |
| 4,979,499 A | 12/1990 | Sun | |
| 5,065,738 A * | 11/1991 | Van Dam | 600/185 |
| 5,438,976 A * | 8/1995 | Nash | 600/186 |
| 5,536,245 A | 7/1996 | Dahlbeck | |
| 5,656,014 A * | 8/1997 | Rooney et al. | 600/240 |
| 5,776,053 A * | 7/1998 | Dragisic et al. | 600/195 |
| 5,993,383 A * | 11/1999 | Haase | 600/191 |

OTHER PUBLICATIONS

Panduit Publication, pp. 1-2, 1999.*

* cited by examiner

*Primary Examiner*—Linda C Dvorak
*Assistant Examiner*—Matthew J Kasztejna
(74) *Attorney, Agent, or Firm*—Clyde I. Coughenour

(57) ABSTRACT

A tongue stabilizer includes a tongue-engaging plate that is held on a laryngoscope blade by pressure sensitive adhesive, with a foam strip in-between to compensate for any irregularities between the tongue-engaging plate and the laryngoscope blade. The tongue-engaging plate is cup shape to cradle the tongue to prevent the tongue from interfering with the visibility and process of intubation. A protective strip can be used to cover the adhesive.

17 Claims, 1 Drawing Sheet

TONGUE STABILIZER FOR LARYNGOSCOPE BLADE

BACKGROUND OF THE INVENTION

1. Field of the Invention

A disposable tongue stabilizer is adhesively attached to a laryngoscope blade to position the tongue during intubation.

2. Description of Related Art

In many emergency situations in order to save lives or give anesthetics for surgery in operating rooms, physicians have to use intubation procedures to establish an artificial airway. During these intubation procedures laryngoscopes are used by physicians as an instrument to keep the tongue out of the way in order to visualize the epiglottis so that an endotracheal tube can be inserted into the trachea.

The problem is that all the laryngoscope blades on the market now are narrow and can hold only approximately half of the tongue, so that it is very hard to make the tongue stay on the laryngoscope blade with any degree of stability. The epiglottis is very difficult to visualize and the endotracheal tube is very hard to insert into the trachea as the tongue gets in the way.

If the patent has a cardiac or respiratory arrest, the critical period is four minutes, and quite often the tube cannot be placed into the trachea within that critical time period. Consequently, the patient will have needless suffering, from irreversible brain damage, or death can occur.

It is old in the art to control the tongue while working in the mouth. G. Hull (U.S. Pat. No. 2,723,662, issued 15 Nov. 1955), and A. Pagoto (U.S. Pat. No. 2,765,785, issued 9 Oct. 1956), and M. Inoue (U.S. Pat. No. 4,589,848, issued 20 May 1986) are examples of tongue depressors. D. Van Dam (U.S. Pat. No. 5,065,738, issued 19 Nov. 1991) and J. Nash (U.S. Pat. No. 5,438,976, issued 8 Aug. 1995) and S. Dahibeck (U.S. Pat. No. 5,536,245, issued 16 Jul. 1996) are examples of using adhesive to secure protective padding or a sensor to laryngoscope blades. W. Sun (U.S. Pat. No. 4,834,077, issued 20 May 1989 and U.S. Pat. No. 4,979,499, issued 25 Dec. 1990) are examples of laryngoscope blade sheaths used to position the tongue during intubation.

SUMMARY OF THE INVENTION

In view of the many different types of blades used, it is difficult to quickly provide an appropriate device on a blade to control the tongue as the intubation process is performed. Rather than providing individual tongue control for each type blade, a universally useable spoon-shaped tongue control is provided. A tongue holder or stabilizer is provided with a pressure-sensitive adhesive support for adhering the tongue holder on any shape blade. The appropriate size tongue control is selected and adhesively attached to the blade at the appropriate location for the individual being treated.

DESCRIPTION OF THE PREFERRED EMBODIMENTS

Figures 1, 2:
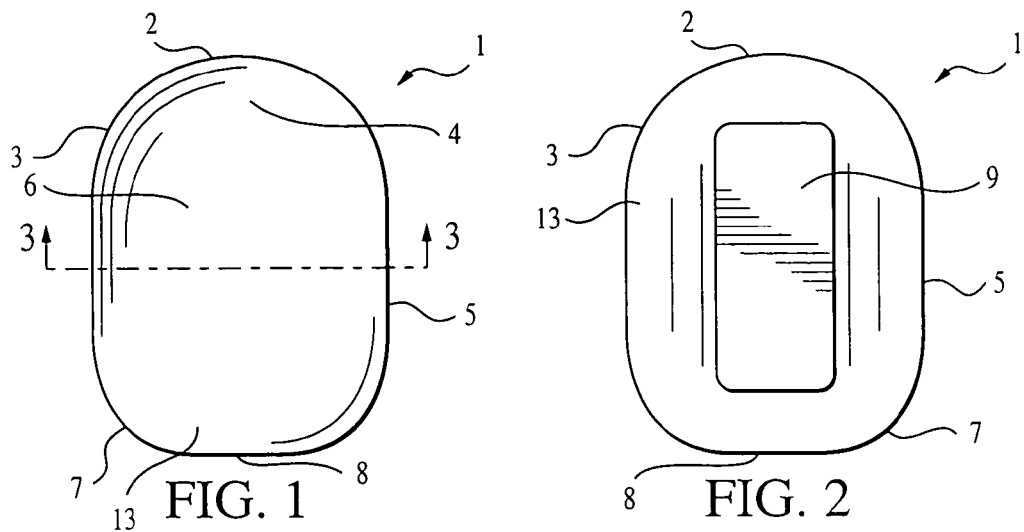
FIG. 1 is a top view of the tongue stablizer.
FIG. 2 is a bottom view of the tongue stabilizer of FIG. 1.

The tongue stabilizer is shown in FIGS. 1-5. FIG. 1 is a top view of the tongue stabilizer 1 showing a front end 2, front side curve 3, upturned front end 4, side 5, concave central area 6, rear side curve 7 and rear or back end 8 of a tongue-engaging plate 13.

FIG. 2 is a bottom view of the tongue stabilizer 1 additionally showing the adhesive protective covering or release material 9.

Figure 3:
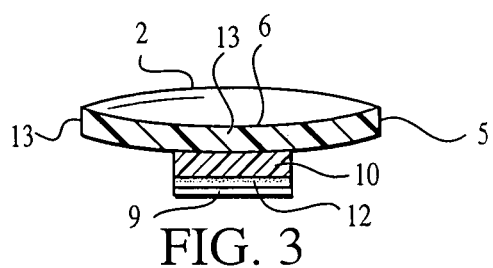
FIG. 3 is an end sectional view of the tongue stabilizer along the lines 3-3 of FIG. 1.

FIG. 3 is a cross-sectional view taken along the section lines 3-3 of FIG. 1. The adhesive-securing configuration can be seen wherein a foam layer 10 is secured to the tongue stabilizer on one inner surface with an adhesive layer 12 adhered to its second outer surface. To protect the adhesive prior to use, a protective film 9 is held over the adhesive. The upturned front end 2 can be seen as well as the concave or spoon-shape central area 6 with upward extending side edges 5.

Figure 4:
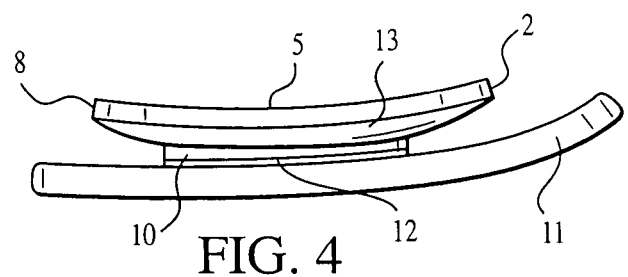
FIG. 4 is a side view of the tongue stabilizer adhered to a laryngoscope blade.

FIG. 4 is a side view of the tongue stabilizer adhesively secured to a laryngoscope blade 11 showing the front end 2, rear end 8 and side 5 with the concave or spoon shape visible as well as the foam support 10 and adhesive 12 bonding it to the blade 11.

Figure 5:
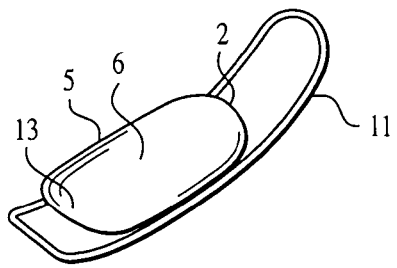
FIG. 5 is a perspective view of the tongue stabilizer adhered to a laryngoscope blade.

FIG. 5 is a perspective view of the tongue stabilizer of FIG. 4, again showing the concave or spoon-shape central area 6.

The tongue stabilizer has a tongue-engaging plate 13 that is in the general shape of an elongated plate with rounded front or distal end and corners rounded to reduce sharp areas at the back or proximal end. The preferred shape of the support is that of a spoon shape or with a concave upper surface to cradle the tongue. The plate preferably has a thickness of from 0.015 to 0.125 inches and a width that extends beyond the width of the supporting laryngoscope blade it is secured to. A width of from ⅞ to 1½ inches and a length of 1 to 2½ inches is satisfactory for most applications. While a flat plate can function adequately to confine the tongue and prevent it from slipping and obstructing and/or obscuring the throat passage, a spoon shape is preferred as it tends to cradle the tongue and hold it within the concavity of the tongue-engaging plate. The preferred depth of the concavity below the front and sides of the plate is ⅛ to ½ inch. The plate can be a stiff paper or metal but an inert non-toxic plastic is preferred.

A foam 10 is secured to the plate by an adhesive or other bonding means that has a more permanent holding power than the blade-securing, pressure-sensitive adhesive 12. The foam padding 10 provides for holding the convex bottom surface of the plate to a different curvature blade 11 along its entire extent by compressing in the areas the plate and blade are closest together. By providing holding power along the entire length of the foam 10 and adhesive 12 a firm bond is established to prevent accidental separation of the tongue stabilizer and blade. The preferred thickness of the foam is from 1/32 to ¼ inch. The foam can be any open or closed pore foam that is inert or non-toxic to body fluids or other materials being used. The foam strip is preferably from ¼ to ½ inch wide and from ¾ to 2 inches long.

The adhesive 12 can be any pressure-sensitive adhesive, having a holding power sufficient to secure the plate under the forces encountered during the intubation process, that is inert and non-toxic while being capable of forcefully releasing the blade 11 from the stabilizer 1 after the procedure is completed. The protective cover 9 can be any of the easily removed plastic or release papers in common use.

When intubation is to be performed, the technician can rapidly review the size blade and plate adequate to perform the procedure, select the blade and plate, remove the protective cover from the adhesive, secure the tongue stabilizer to the blade and proceed with the procedure using the plate to confine the tongue while intubating.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

The invention claimed is:

1. A tongue stabilizer for a laryngoscope blade comprising:
    a tongue-engaging plate having a top surface, a bottom surface, a forward end, a rear end, a first side, a second side and a central area;
    a foam strip support having a top surface and a bottom surface with said foam top surface attached to said tongue engaging plate bottom surface between said forward end and said rear end and between said first side and said second side;
    a pressure-sensitive adhesive having a top surface, attached to and extending along said foam support bottom surface, and a bottom surface, available for attaching said tongue stabilizer to a laryngoscope blade.

2. A tongue stabilizer for a laryngoscope blade as in claim 1 wherein:
    said tongue-engaging plate forward end is rounded and said rear end and said first side meet in a rounded corner and said rear end and said second side meet in a rounded corner.

3. A tongue stabilizer for a laryngoscope blade as in claim 2 wherein:
    said tongue-engaging plate width between said first side and said second side is between ⅞ to 1½ inch so as to extend externally beyond the laryngoscope blade;
    said tongue-engaging plate length between said forward end and said rear end is from 1 to 2½ inches long.

4. A tongue stabilizer for a laryngoscope blade as in claim 3 wherein:
    said tongue-engaging plate has a thickness of from 0.015 to 0.125 inch.

5. A tongue stabilizer for a laryngoscope blade as in claim 4 wherein:
    said tongue engaging plate top central area is recessed to provide a tongue-cradling concavity;
    said tongue-engaging plate top surface central area is recessed below said forward end, rear end, first side and second side a distance of from ⅛ to ½ inch.

6. A tongue stabilizer for a laryngoscope blade as in claim 1 wherein:
    said tongue engaging plate top central area is recessed to provide a tongue-cradling concavity.

7. A tongue stabilizer for a laryngoscope blade as in claim 6 wherein:
    said tongue-engaging plate top surface central area is recessed below said forward end, rear end, first side and second side from a distance of ⅛ to ½ inch.

8. A tongue stabilizer for a laryngoscope blade as in claim 1 wherein:
    said tongue-engaging plate has a thickness of from 0.015 to 0.125 inch.

9. A tongue stabilizer for a laryngoscope blade as in claim 1 wherein:
    said tongue-engaging plate width between said first side and said second side is between ⅞ to 1½ inch so as to extend externally beyond the laryngoscope blade.

10. A tongue stabilizer for a laryngoscope blade as in claim 1 wherein:
    said tongue-engaging plate length between said forward end and said rear end is from 1 to 2½ inches long.

11. A tongue stabilizer for a laryngoscope blade as in claim 1 wherein:
    said foam strip has a thickness of from 1/32 to ¼ inch.

12. A tongue stabilizer for a laryngoscope blade as in claim 11 wherein:
    said foam strip has a width from ¼ to ½ inch and a length of from ¾ to 2 inches.

13. A tongue stabilizer for a laryngoscope blade as in claim 12 wherein:
    said tongue-engaging plate forward end is rounded and said rear end and said first side meet in a rounded corner and said rear end and said second side meet in a rounded corner;
    said tongue-engaging plate has a thickness of from 0.015 to 0.125 inch;
    said tongue-engaging plate width between said first side and said second side is between ⅞ to 1½ inch so as to extend externally beyond the laryngoscope blade;
    said tongue-engaging plate length between said forward end and said rear end is from 1 to 2½ inches long.

14. A tongue stabilizer for a laryngoscope blade as in claim 13 wherein:
    said tongue engaging plate top central area is recessed to provide a tongue-cradling concavity.

15. A tongue stabilizer for a laryngoscope blade as in claim 14 wherein:
    a protective covering is on said pressure-sensitive adhesive bottom surface to protect it from contamination.

16. A tongue stabilizer for a laryngoscope blade as in claim 15 wherein
    said tongue-engaging plate top surface central area is recessed below said forward end, rear end, first side and second side a distance of from ⅛ to ½ inch.

17. A tongue stabilizer for a laryngoscope blade as in claim 1 wherein:
    a protective covering on said pressure-sensitive adhesive bottom surface to protect it from contamination.

* * * * *